United States Patent
Mower

(10) Patent No.: US 10,940,318 B2
(45) Date of Patent: Mar. 9, 2021

(54) METHOD AND APPARATUS FOR ELECTRICAL CURRENT THERAPY OF BIOLOGICAL TISSUE

(71) Applicant: Morton M. Mower, Denver, CO (US)

(72) Inventor: Morton M. Mower, Denver, CO (US)

(73) Assignee: Morton M. Mower, Denver, CO (US)

( * ) Notice: Subject to any disclaimer, the term of this patent is extended or adjusted under 35 U.S.C. 154(b) by 0 days.

(21) Appl. No.: 14/740,681

(22) Filed: Jun. 16, 2015

(65) Prior Publication Data

US 2015/0360025 A1    Dec. 17, 2015

Related U.S. Application Data

(60) Provisional application No. 62/013,126, filed on Jun. 17, 2014.

(51) Int. Cl.
| | | |
|---|---|---|
| *A61N 1/365* | (2006.01) | |
| *A61N 1/32* | (2006.01) | |
| *A61N 1/362* | (2006.01) | |
| *A61N 1/36* | (2006.01) | |

(52) U.S. Cl.
CPC .............. *A61N 1/365* (2013.01); *A61N 1/32* (2013.01); *A61N 1/3628* (2013.01); *A61N 1/326* (2013.01); *A61N 1/36002* (2017.08); *A61N 1/36007* (2013.01); *A61N 1/36121* (2013.01); *A61N 1/36164* (2013.01)

(58) Field of Classification Search
CPC . A61N 1/00; A61N 1/05; A61N 1/362; A61N 1/365; A61B 5/00; A61B 5/0402
USPC ............. 600/509, 510; 607/4, 9, 123
See application file for complete search history.

(56) References Cited

U.S. PATENT DOCUMENTS

| | | | |
|---|---|---|---|
| 3,757,791 A | | 9/1973 | Berkovits |
| 4,738,250 A | * | 4/1988 | Fulkerson ............ A61N 1/326 607/50 |
| 5,817,138 A | * | 10/1998 | Suzuki ................. A61N 1/323 607/67 |
| 5,871,506 A | | 2/1999 | Mower |

(Continued)

FOREIGN PATENT DOCUMENTS

| | | |
|---|---|---|
| JP | 2003-517327 A | 5/2003 |
| JP | 2004-523312 A | 8/2004 |

(Continued)

OTHER PUBLICATIONS

Stefano Pietronave, et al. "Monophasic and Biphasic Electrical Stimulation Induces a Precardiac Differentiation in Progenitor Cells Isolated from Human Heart" Stem Cells and Development, vol. 23, No. 8, 2014, 12 pages, from Italy.

(Continued)

*Primary Examiner* — Catherine M Voorhees
*Assistant Examiner* — Roland Dinga
(74) *Attorney, Agent, or Firm* — Oblon, McClelland, Maier & Neustadt, L.L.P.

(57) ABSTRACT

A method and device for performing electrical current therapy on biological tissue. The device can operate continuously as a bio-energetic thermostat to continuously provide electrical current therapy, or based on sensing parameters and providing electrical current therapy only when the parameters indicate that the electrical current therapy is to be applied.

15 Claims, 2 Drawing Sheets

(56) References Cited

U.S. PATENT DOCUMENTS

| | | | |
|---|---|---|---|
| 5,919,216 A * | 7/1999 | Houben | A61B 5/14532 |
| | | | 607/72 |
| 6,067,470 A | 5/2000 | Mower | |
| 6,136,019 A | 10/2000 | Mower | |
| 6,141,587 A | 10/2000 | Mower | |
| 6,178,351 B1 | 1/2001 | Mower | |
| 6,292,695 B1 * | 9/2001 | Webster, Jr. | A61N 1/0563 |
| | | | 607/113 |
| 6,295,470 B1 | 9/2001 | Mower | |
| 6,332,096 B1 | 12/2001 | Mower | |
| 6,345,198 B1 | 2/2002 | Mouchawar et al. | |
| 6,411,845 B1 * | 6/2002 | Mower | A61N 1/3622 |
| | | | 607/5 |
| 6,411,847 B1 | 6/2002 | Mower | |
| 6,535,767 B1 | 3/2003 | Kronberg | |
| 6,895,274 B2 | 5/2005 | Mower | |
| 7,440,800 B2 | 10/2008 | Mower | |
| 7,908,003 B1 | 3/2011 | Mower | |
| 8,285,378 B1 | 10/2012 | KenKnight et al. | |
| 8,290,585 B2 | 10/2012 | Mower | |
| 8,447,399 B2 | 5/2013 | Mower | |
| 2004/0049235 A1 | 3/2004 | Deno et al. | |
| 2004/0116994 A1 | 6/2004 | De Bellis | |
| 2005/0004621 A1 * | 1/2005 | Boveja | A61N 1/08 |
| | | | 607/45 |
| 2006/0142817 A1 * | 6/2006 | Chandler | A61N 1/32 |
| | | | 607/50 |
| 2007/0129776 A1 | 6/2007 | Robins et al. | |
| 2008/0319496 A1 * | 12/2008 | Zhu | A61N 1/3627 |
| | | | 607/5 |
| 2010/0331916 A1 * | 12/2010 | Parramon | A61B 5/04001 |
| | | | 607/60 |
| 2012/0029587 A1 * | 2/2012 | Zhou | A61N 1/36114 |
| | | | 607/17 |
| 2014/0350624 A1 | 11/2014 | Mower | |
| 2014/0350625 A1 | 11/2014 | Mower | |
| 2014/0350626 A1 | 11/2014 | Mower | |
| 2014/0350627 A1 | 11/2014 | Mower | |
| 2014/0350628 A1 | 11/2014 | Mower | |
| 2014/0350629 A1 | 11/2014 | Mower | |

FOREIGN PATENT DOCUMENTS

| | | |
|---|---|---|
| JP | 2005-501617 A | 1/2005 |
| JP | 2007-503907 A | 3/2007 |
| JP | 2007-532178 A | 11/2007 |
| JP | 2008-501439 A | 1/2008 |
| RU | 2 290 442 C2 | 12/2006 |
| RU | 2 312 691 C1 | 12/2007 |
| WO | WO 97/25098 | 7/1997 |
| WO | WO 98/10828 | 3/1998 |
| WO | WO 99/44682 A1 | 9/1999 |
| WO | WO 01/82771 A2 | 11/2001 |
| WO | WO 02/070065 A2 | 9/2002 |
| WO | WO 03/020364 A2 | 3/2003 |
| WO | WO 2005/023081 A2 | 3/2005 |
| WO | WO 2005/102450 A1 | 11/2005 |
| WO | WO 2005/120635 A1 | 12/2005 |

OTHER PUBLICATIONS

Loraine L. Y. Chiu, et al. "Biphasic Electrical Field Stimulation Aids in Tissue Engineering of Multicell-Type Cardiac Organoids" Tissue Engineering: Part A, vol. 17, Nos. 11 and 12, 2011, pp. 1465-1477, from Toronto.

Supplementary European Search Report dated Feb. 13, 2018 in European Patent Application No. 15 809 234.6, citing documents AO-AQ therein, 6 pages.

Office Action dated Mar. 29, 2018 in Russian Patent Application No. 2016146519, with English-language Translation, 9 pages. (The references cited therein were previously cited by the Examiner.).

Search Report dated Mar. 29, 2018 in Russian Patent Application No. 2016146519, citing documents AR-AS therein, with English-language Translation, 5 pages.

Office Action dated Aug. 21, 2018 in corresponding Russian Patent Application No. 2016146519/14(074658) (with English Translation), 12 pages.

Combined Chinese Office Action and Search Report dated Jul. 27, 2018 in Patent Application No. 201580032111.3 (with English language translation).

Israeli Office Action dated Jul. 29, 2018 in Israeli Patent Application No. 248980, 2 pages.

Office Action dated Mar. 26, 2019 in the corresponding Japanese Patent Application No. 2016-573025 with English Translation citing documents AA, and AM—AX therein 19 pages.

Chinese Office Action dated Apr. 2, 2019 in Patent Application No. 201580032111.3, 26 pages (with English translation).

Office Action dated Sep. 30, 2019 in Indian Patent Application No. 201617040049, 7 pages. (The references cited therein were previously cited.).

Office Action dated Aug. 1, 2019 in Russian Patent Application No. 2016146519/14(074658), citing documents AA-AC therein, with English-language translation, 19 pages.

Office Action dated Sep. 2, 2019 in Chinese Patent Application No. 201580032111.3, with English-language translation, 20 pages. (The references cited therein were previously cited.).

Office Action dated Sep. 25, 2019 in Australian Patent Application No. 2015277177, 3 pages. (The references cited therein were previously cited.).

Japanese Office Action dated Jan. 7, 2020, in Patent Application No. 2016-573025, 9 pages (with English translation).

Office Action dated Sep. 1. 2020 in Canadian Application No. 2,947,056.

Office Action dated Nov. 3, 2020 in Israeli Application No. 248980.

Song, B., Gu, Y., Pu, J. et al. "Application of direct current electric fields to cells and tissues in vitro and modulation of wound electric field in vivo" Nat Protoc 2. 1479-1489 (2007). https.//doi.org/10.1038/nprot.2007.205 (abstract only).

\* cited by examiner

METHOD AND APPARATUS FOR ELECTRICAL CURRENT THERAPY OF BIOLOGICAL TISSUE

CROSS-REFERENCE TO RELATED APPLICATION(S)

This application claims priority to U.S. Provisional Application No. 62/013,126, filed Jun. 17, 2014, the entire contents of which are incorporated herein by reference.

FIELD

The present disclosure relates to a method and apparatus for treating biological tissue using electrical current. For example, aspects of the present disclosure relate to a method and apparatus for treating and preconditioning damaged myocardial tissue, for influencing the behavior of stem cells, for increasing production of insulin by pancreatic tissue, for increasing production of glucagon and other small molecule products of the pancreas, for increasing cellular production of ATP, for reinvigorating aging cells and for preventing and treating cancer by applying an electrical current, which can be anodal or biphasic, to the appropriate tissue and cells.

BACKGROUND

The "background" description provided herein is for the purpose of generally presenting the context of the disclosure. Work of the named inventor, to the extent it is described in this background section, as well as aspects of the description which may not otherwise qualify as prior art at the time of filing, are neither expressly or impliedly admitted as prior art against the present disclosure.

While it is known that each cell in the human body has a membrane potential, it is not well-appreciated what its function might be, and that some cells in the body aside from heart and nerve cells, depolarize. For example, at one extreme, patients with an implantable cardioverter defibrillator (ICD) may face a problem of the ICD not firing because no arrhythmias are present. These patients who appear to require no stimulation likely do so due to a naturally more vigorous membrane potential. That is, increased membrane potential is protective against arrhythmias.

On the other hand, as certain cells age, their membrane potential decreases and their function can deteriorate in many important areas of the body. For instance, cells in the myocardium do not conduct impulses as rapidly as normal. Thus, the slow conduction can produce arrhythmias by giving rise to re-entrant rhythms, early and late afterdepolarizations, and decremental conduction.

In addition, the diseases of mitochondrial dysfunction are associated with impaired membrane potential in many cells and are a generalized form of impaired membrane potential. This gives rise to serious multi-organ dysfunctions including brain as well as heart abnormalities. Such patients often experience conduction defects which manifestation may be cured by a pacemaker even though the abnormalities of other affected parts of the body are not helped.

Even in patients without generalized mitochondrial dysfunction, low membrane potentials in the arteries are associated with impaired metabolism, switching from aerobic to anaerobic mechanisms, and excess production of peroxidases and reactive oxygen species. These changes are associated with increased atherosclerosis.

Depolarization in areas other than heart and nerve tissue is poorly appreciated as in the Beta cell in the pancreas where depolarization initiates the secretion of insulin. This occurs in two phases. An initial phase lasts 5 minutes and is initiated by closure of ATP-sensitive potassium channels. When the pancreas sees a glucose molecule, electrons get stripped from it and get passed down the electron transport chain thereby converting ADT to ATP. This is seen by the cell and the ATP-sensitive potassium channels close causing the depolarization of the Beta cell. This phenomenon causes the granules of insulin in the cytoplasm to migrate towards, and fuse with, the inner membrane of the cell. A pore then forms and the insulin gets extruded into the circulation. A second phase of insulin production lasts from about half an hour to two hours and is less-well understood, but is somehow related to calcium channels. Theoretically, one could force depolarization of the Beta cell with cathodal currents since these also reduce the membrane potential until the threshold for depolarization is reached. On the other hand, the role of anodal current does not appear to have been previously appreciated or investigated, and seems to be more related to insulin production.

In another area, myocardial damage generally due to heart attacks leads to impairment of cardiac function which can seriously impair longevity and quality of life. Generally, only supportive care is given to the patient to allow scar tissue formation in the damaged area. However, attempts to limit the damage have been tried by infusing intravenously massive amounts of stem cells with the hope that some will implant into the damaged area, differentiate into functioning myocytes, and limit the loss of contractility. However the cells often do not line up properly, or may form a geometry which promotes reentrant circuits and can result in lethal arrhythmias. The stimuli controlling the stem cell functioning are poorly understood, and have not hitherto included electrical phenomena.

SUMMARY

In one inventive aspect, a method for performing electrical current therapy on biological tissue includes administering the electrical current therapy to the biological tissue.

In another inventive aspect, a device for providing electrical current therapy to biological tissue, includes a generator circuit configured to generate the electrical current therapy administered to the biological tissue via at least one electrode.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
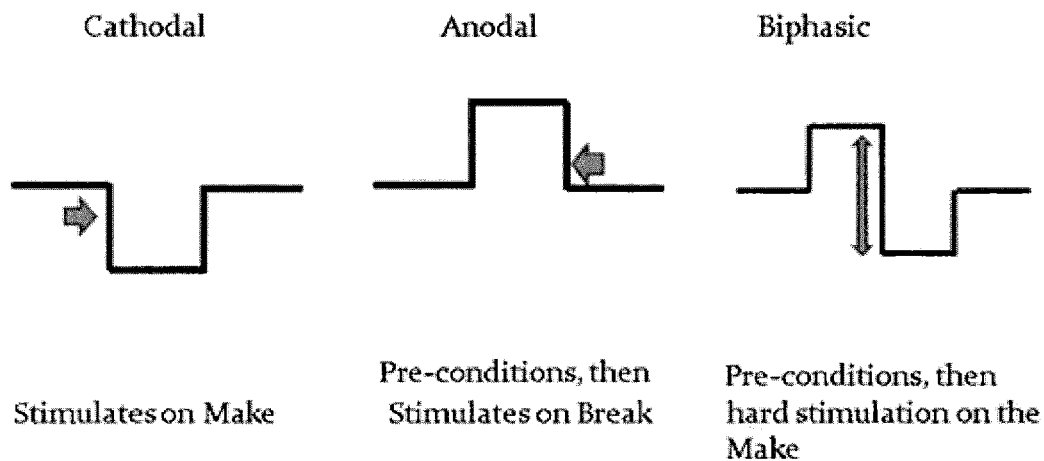
FIG. 1 depicts waveforms for electrical current stimulation according to exemplary aspects of the present disclosure.

The following descriptions refer to the drawings, wherein like reference numerals designate identical or corresponding parts throughout the several views.

When cardiac pacing is performed in a bipolar configuration, the cathode (negatively charged electrode) is in contact with the myocardium and the anode (positively charged electrode) lies more proximal in the blood pool. Also, myocardial stimulation by the pacing stimulus typically occurs only at the interface with the cathode because, given equal sized electrodes, anodal stimulation has a higher threshold compared to cathodal stimulation except for a "dip" at short coupling intervals and the anode usually has an electrode with a larger surface area making stimulation less likely.

Anodal stimulation was initially mistakenly implicated as a cause of arrhythmias, especially in conditions of electrolyte imbalance or ischemia. However, the arrhythmogenesis was primarily related to pacing at a short coupling interval that could occur with older asynchronous pacemakers and may not be an issue with the current devices where pacing almost always occurs in a demand mode. Further, anodal stimulation tends to improve conduction velocity and mechanical performance in the heart, thereby making it a desirable alternative.

FIG. 1 illustrates different waveforms that may be utilized for electrically stimulating biological tissue such as the heart. As shown in FIG. 1, anodal stimulation stimulates on the "break" or trailing edge of the pulse, whereas cathodal stimulation is configured to operate on the "make" or leading edge of the pulse. Specifically, anodal stimulation includes a pre-conditioning stage after which stimulation occurs on the falling edge of the positive clock pulse. On the other hand, as shown in FIG. 1, cathodal stimulation occurs on the initial edge of a negative clock pulse. Further, FIG. 1 also depicts a biphasic pulse that creates a maximum total voltage difference between the positive peak and the negative peak greater than either the anodal or cathodal stimulation pulses alone. This peak to peak voltage being of greater magnitude than the anodal and cathodal counterparts drives the membrane potential swiftly past the stimulation threshold, thus giving the strongest possible depolarization pulse. This explanation is given in terms of stimulation pulses for clarity. However, the principles described are applicable to any currents or waveforms used in electrical current therapy, whether stimulating or not, as one of ordinary skill would recognize.

As first recognized by the present inventor, pacing with an anodal component has definite usefulness. For instance, pacing stem cells in a petri-dish with an anodal or biphasic current pulse results in the cells being lined up along the lines of electrical flux as well as those cells multiplying and being differentiated rapidly. Pacing stem cells with anodal currents, for example, cause the stem cells to migrate towards the anodal potential. Thus, electrical current therapy may be used to improve stem cell alignment and aid in long-term healing of damaged tissue since the stem cells applied to the damaged tissue are applied with better alignment, and since the stem cells multiply and differentiate more quickly as a result of the electrical current therapy.

In what follows, a description of an implantable device used for electrical current therapy according to exemplary aspects of the present disclosure is first provided. Then several applications of the device in different scenarios are provided.

Figure 2:
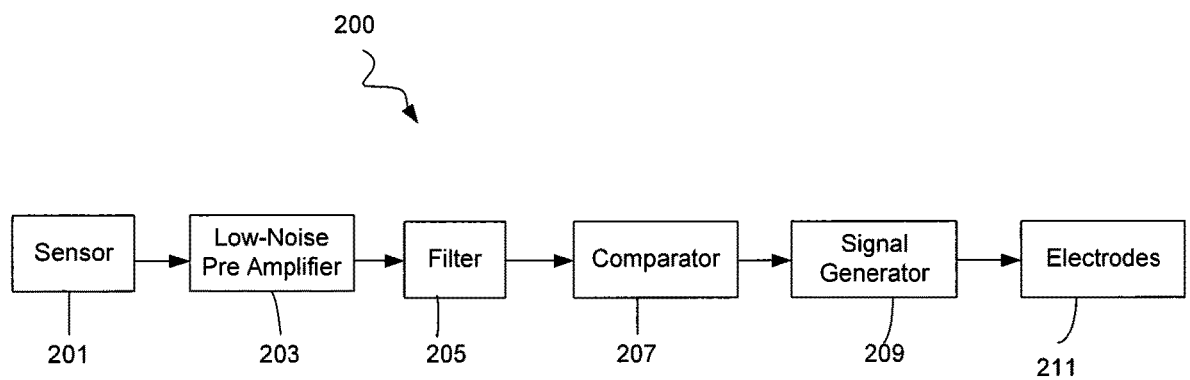
FIG. 2 illustrates a block diagram of an implantable device according to exemplary aspects of the present disclosure.

FIG. 2 illustrates a block diagram 200 of an implantable device that may be used for providing electrical current therapy to malfunctioning organs. The implantable device 200 includes a sensor 201, a low noise preamplifier 203, a filter 205, a comparator 207, a signal generator 209 and electrodes 211.

The sensor 201 may be configured to sense rhythm and contractions of the heart as well as membrane potential of the myocardial and/or other cells in other organs. The sensors 201 may include atrial sensors, ventricular sensors or the like, but can also include any sensor located on, in or proximate to living tissue. The data captured by the circuitry in sensor 201 is amplified by the circuitry of the low noise pre-amplifier 203. Further, the amplified data may be passed through circuitry of a second order low noise filter to achieve an appropriate signal, such as an ECG signal in the cause of the heart. The signal from the filter is provided to the comparator 207. The circuitry of the comparator may implement a threshold detector, to detect a heart beat event executed by the heart, or alternatively, such as when used on other organs of the body, the circuitry of comparator may detect if the voltage potential of the cells is below a predetermined threshold. The output of the comparator 207 is input to the circuitry of the signal generator 209 that may be configured to generate a signal of a particular shape such as a square wave pulse, a saw tooth waveform or the like. The signal from the signal generator 209 is applied to the circuitry of the electrodes 211 to provide anodal, biphasic or cathodal current therapy. As can be appreciated such therapy may include pacing of the heart, but this need not be the only application. The current therapy may be provided to other organs and/or tissue without departing from the scope of the present disclosure. Furthermore, a low power consumption microcontroller that includes processing and memory circuits may be utilized to control the overall operation of the implantable device.

Though the above description refers to the device as "implantable," the device may also be one that remains outside the body, i.e., a device that is not implantable. Therefore, the term "implantable" is to be considered as exemplary rather than limiting upon the present disclosure.

According to an exemplary embodiment, placing anodal currents on the outside of cells increases the membrane potential, and, as first recognized by the present inventor, such an effect may last for a number of hours. The application of anodal currents also gives rise to an increased production of adenosine tri-phosphate (ATP) which is further used for the work of the cell.

There are innumerable uses for improvements in the functioning of cells. For instance, there are cells in the body which can easily be obtained from the body and easily be given back at a later time. White blood cells (WBCs) are present in blood intended for blood transfusions. These cells can be hyperpolarized by applying an anodal current to the blood transfusion packet. Such "super" WBCs when transfused back into the body will have increased ability to fight infections, especially important in severe life-threatening sepsis. Further, another usefulness of anodal conditioning is in improving the length of telomeres at the end of the chromosomes. Specifically, cell cultures can only be sub-cultured for a limited number of times because as they age, the telomeres at the end of the chromosomes become shorter until they no longer grow in the sub-culture. However, as first recognized by the present inventor, exposing such cells to anodal, biphasic or cathodal current therapy causes the telomeres to be lengthened and the vigor of the culture restored. Note that the membrane potential can be measured by fluorometry, as for example from WBCs and may serve as a surrogate for what is happening in other tissues as well.

According to another exemplary embodiment, electrical current therapy stimulates hormone production in endocrine tissues, which may lead to treatment of the various forms of diabetes. For example, types I and II diabetes probably have different etiologies. In some patients there is certainly islet cell destruction with much less insulin production, while in others there may be a defect in the mechanism of insulin secretion. For example, the first defect that may be detected in pre-diabetes is a blunting of the first 5-minute surge of insulin secretion. Increasing the membrane potential of the beta cell by anodal, biphasic or cathodal currents can produce useful results by correcting this blunting.

The application of anodal, biphasic or cathodal also current increases the membrane potential thereby producing more ATP. Such an application of electrical current therapy can have many implications from a therapeutic standpoint. Firstly, diabetes may be ameliorated by applying current to the pancreas. This can be achieved by passing a lead through the common bile duct and causing it to lie within the head of the pancreas. Alternatively, a small screw-in lead could be directly applied to the pancreas through a tiny laparoscopic incision. This process could be used for applying current waveforms of many types, some stimulating production of insulin without affecting the normal endogenous secretion control mechanism and other waveforms starting secretion by starting depolarization of the islet cells.

Furthermore, according to another exemplary embodiment, another use of electrical current therapy is directed towards pancreatic tissues that are to be used for transplantation. Generally, such a tissue is placed in a "protected site", such as under the renal capsule. A problem the transplants surgeons commonly face is that of not knowing the viability of the cells, or how effectively they can produce insulin. However, anodal, biphasic or cathodal current may be applied to the proposed tissue and the insulin produced can be measured. Then, the cells may be stimulated to have a higher membrane potential which "up-regulates" insulin production and makes for a more active and better transplant. As one of ordinary skill would recognize, similar electrical current therapy may also be applied to virtually all endocrine tissues of the body.

According to another exemplary embodiment, anodal and biphasic pacing pulses can speed conduction down the myocardium and increase contractility. Patients whose sites were paced with both cathodal and anodal polarities simultaneously had a much faster rate of improvement of congestive heart failure than those paced simultaneously with only the cathodal polarity. Thus, there are useful properties of anodal polarity beyond just higher thresholds.

Anodal polarity increases the membrane potential of the heart cells so that when the cells do depolarize, they do so from a more electronegative level, more sodium channels become available, the action potential is more vigorous and travels faster, and more calcium exchanges for the sodium enhancing contractility. Further, the improved cardiac function with the biphasic waveform appears to result from more than just improving hemodynamics. For instance, there seems to be an additional mechanism influencing the functioning of the small numbers of naturally present stem cells in the body. The function of these cells appears to be that they are delivered to damaged areas in the body in an attempt to repair them.

As an example, a number of types of cell cultures in Petri dishes, including mature and immature fibrocytes, were subjected to pacing across the Petri dishes. The cells were found to line up along the lines of electrical flux and to divide and differentiate more rapidly. Furthermore, the membrane potential of the cells increased and lasted for several hours. ATP levels were found to be increased due to the anodal component of the waveforms. The protein array within paced cells was found to be radically different from un-paced cells indicating marked up and down-regulation of many intra-cellular proteins.

According to another exemplary embodiment, electrical current therapy may be utilized to promote angiogenesis for vascularizing transplant tissues. For instance, blood vessels slightly larger than capillaries but smaller than arterioles can be cultured in cell culture media. Those which originated from small animals such as mice and rabbits can be stimulated pharmacologically so as to divide and form a network of vessels. When transplant tissue is added, it gets vascularized and gives rise to a transplant tissue with its own blood vessels for nourishment. This implanted tissue does very well.

For some reason, human small vessel cell cultures cannot be stimulated in this pharmacologically to grow blood vessels and, as a result, cannot be used to improve tissues intended for transplant. Thus, using anodal, biphasic or cathodal current to produce ATP to increase metabolism artificially and to augment cellular functions can bypass the block in the usual pathway of stimuli and produce the desired result by an alternate route, allowing this technique of improving transplant viability to be extended to human tissue as well.

Further, electrical current therapy can be promoted to up-regulate functioning of suppressor oncogenes to suppress cancer growth. One of the mechanisms by which cancer is thought to arise is by loss of the ability of certain tumor-suppressing parts of DNA (oncogenes) to function sufficiently. This is but one of the cellular functions which can be stimulated back to normal by exposing cells to anodal current, creating ATP at virtually no cost to the cell, repairing the cell, increasing its resistance to becoming cancerous, and likely even causing regression of existing tumors.

Figure 3:
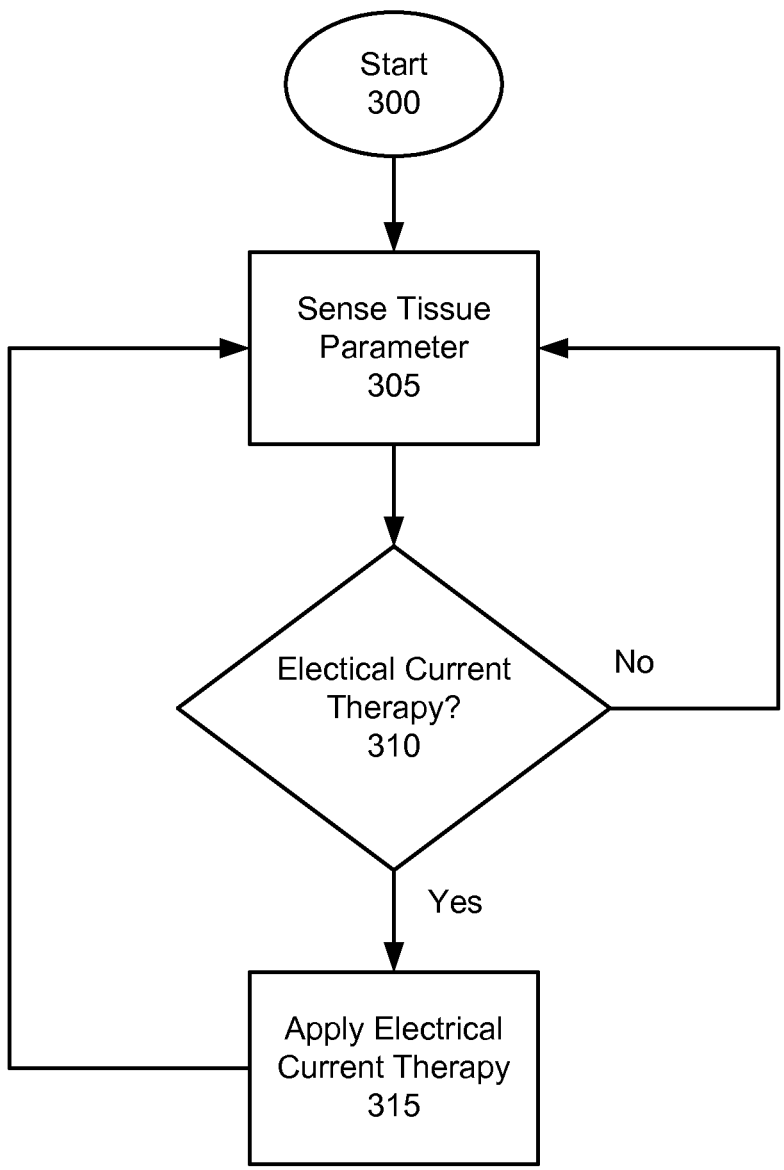
FIG. 3 is a flowchart of a method for applying electrical current therapy to tissue according to exemplary aspects of the present disclosure.

Next, an exemplary method for applying electrical current therapy is described with reference to FIG. 3. In FIG. 3, the method begins at step 300 and moves to step 305 where a parameter of the tissue is sensed to determine whether electrical current therapy is necessary. As discussed above, many parameters may be sensed depending on tissue type, etc. For example, the PQRS waveform of a heart may be sensed. As such the specific tissue parameter sensed should not be viewed as limiting upon the present disclosure. Alternatively, step 305 may be omitted and the electrical current therapy may be provided without prior sensing.

From step 305 the method proceeds to step 310 where the decision to provide electrical current therapy, or not, is made. If no electrical current therapy is deemed necessary, the method reverts to step 305 to continue monitoring the tissue. Alternatively, the method may be allowed to end rather than loop back to the sensing step 305.

If at step 310 it is determined that electrical current therapy should be provided, the method proceeds to step 315 to administer any one of anodal current, biphasic current or cathodal current to the tissue. Then the method reverts to step 305 to determine the efficacy of the treatment by collecting new parameter values to determine whether further electrical current therapy is required.

As one of ordinary skill would recognize, the determination of whether or not to provide electrical current therapy to the tissue may be made by comparing the parameter sensed to a threshold, or a template, or by monitoring the parameter over time to evaluate a trend in the parameter. Other methods of determining whether electrical current therapy should be provided are also possible.

For the sake of simplicity, the above discussion is presented as a sequence of steps that are performed serially.

However, one of ordinary skill would recognize that the steps of FIG. 3 may be performed in parallel, such that the parameter sensing step 305 and the electrical current therapy providing step 315 may happen at the same time. Other orders of performing these steps are also possible without departing from the scope of the present disclosure.

In another exemplary embodiment that is, of course, readily combinable with any aspect of the above-described embodiments, and vice versa, the electrical current therapy is applied to biological tissue without prior, or post, monitoring of the biological tissue for changes. For example, a set waveform for the electrical current therapy can be established beforehand and preprogrammed into an implantable device (or a device that is not implanted). The device can then be connected to the biological tissue via at least one lead and the electrical current therapy is then provided to the biological tissue indefinitely, and without sensing whether any changes are occurring in the biological tissue as a result of the electrical current therapy. That is, the electrical current therapy is provided and continued regardless, or independent of, changes in the biological tissue.

The above-described embodiment can be used to, for example, regulate a bio-energetic thermostat of the biological tissue by continuously providing the electrical current therapy thereto. In other words, the continued application of the electrical current therapy to the biological tissue may rejuvenate its cells (i.e., increase its bio-energy), but such application should be continuous to maintain the increase of bio-energy in the biological tissue. Of course, this is only one example of the device and method according to this embodiment, and other examples are possible without departing from the scope of the present disclosure.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for performing electrical current therapy on biological tissue, comprising:
   pre-programming circuitry with parameters to generate an electrical current therapy having a set predetermined waveform; and
   continuously administering, with the circuitry, the electrical current therapy with the set predetermined waveform to the biological tissue without monitoring the biological tissue for changes after the administering of the electrical current therapy,
   wherein the biological tissue includes pancreatic tissue, and the method further comprises increasing insulin production of the pancreatic tissue by applying the electrical current therapy with the set predetermined waveform to the pancreatic tissue.

2. The method according to claim 1, wherein the set predetermined waveform includes an anodal waveform.

3. The method according to claim 1, wherein the set predetermined waveform includes a cathodal waveform.

4. The method according to claim 1, wherein the set predetermined waveform includes a biphasic waveform.

5. The method according to claim 1, wherein the electrical current therapy with the set predetermined waveform increases Adenotriphosphate (ATP) production in cells of the biological tissue.

6. The method according to claim 1, further comprising increasing mobility of stem cells in the biological tissue via the electrical current therapy with the set predetermined waveform.

7. The method according to claim 1, wherein the biological tissue is a cell culture and the electrical current therapy with the set predetermined waveform is administered to promote growth of the cell culture.

8. The method according to claim 1, wherein the electrical current therapy with the set predetermined waveform is administered to the biological tissue without sensing any biological tissues parameter.

9. The method according to claim 1, wherein the circuitry does not monitor the biological tissue for changes before the administering of the electrical current therapy with the set predetermined waveform.

10. A device for providing electrical current therapy to biological tissue, comprising:
    circuitry configured to
       generate the electrical current therapy with a set predetermined waveform based on pre-programmed parameters, and
       continuously administer the electrical current therapy with the set predetermined waveform to the biological tissue via at least one electrode without monitoring the biological tissue for changes after the administering of the electrical current therapy,
    wherein the biological tissue includes pancreatic tissue, and the circuitry is further configured to increase insulin production of the pancreatic tissue by causing the generator circuit to generate and apply the electrical current therapy with the set predetermined waveform to the pancreatic tissue.

11. The device according to claim 10, wherein the set predetermined waveform includes an anodal waveform.

12. The device according to claim 10, wherein the set predetermined waveform includes a cathodal waveform.

13. The device according to claim 10, wherein the set predetermined waveform includes a biphasic waveform.

14. The device according to claim 10, wherein the electrical current therapy with the set predetermined waveform increases Adenotriphosphate (ATP) production in cells of the biological tissue.

15. The device according to claim 10, wherein the circuitry is further configured to increase mobility of stem cells in the biological tissue by causing the generator circuit to generate and apply the electrical current therapy with the set predetermined waveform to the biological tissue.

* * * * *

UNITED STATES PATENT AND TRADEMARK OFFICE
CERTIFICATE OF CORRECTION

PATENT NO. : 10,940,318 B2
APPLICATION NO. : 14/740681
DATED : March 9, 2021
INVENTOR(S) : Morton M. Mower Page 1 of 1

It is certified that error appears in the above-identified patent and that said Letters Patent is hereby corrected as shown below:

In the Specification

In Column 1, Line 59, delete "not", and;

In Column 2, Line 19, delete "more".

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*